(12) United States Patent
McConnell et al.

(10) Patent No.: US 6,264,612 B1
(45) Date of Patent: Jul. 24, 2001

(54) CATHETER WITH MECHANO-RESPONSIVE ELEMENT FOR SENSING PHYSIOLOGICAL CONDITIONS

(75) Inventors: Keith B. McConnell, West Chester; Colin D. Rudolph, Cincinnati, both of OH (US)

(73) Assignee: Children's Hospital Medical Center, OH (US)

( * ) Notice: Subject to any disclaimer, the term of this patent is extended or adjusted under 35 U.S.C. 154(b) by 0 days.

(21) Appl. No.: 09/483,316

(22) Filed: Jan. 14, 2000

(51) Int. Cl.[7] .................................................. A61B 5/02
(52) U.S. Cl. .................. 600/486; 600/485; 600/488; 600/561
(58) Field of Search .................................. 600/481, 485, 600/486, 488, 561, 585

(56) References Cited

U.S. PATENT DOCUMENTS

| 3,946,724 | * | 3/1976 | La Balme ........................... 73/706 |
| 4,191,193 | * | 3/1980 | Seo ...................................... 600/488 |
| 4,274,423 | | 6/1981 | Mizuno et al. . |
| 4,426,689 | | 1/1984 | Henle et al. . |
| 4,456,013 | * | 6/1984 | De Rossi et al. ................... 600/488 |
| 4,711,249 | * | 12/1987 | Brooks ................................ 600/561 |
| 4,722,348 | | 2/1988 | Ligtenberg et al. . |
| 4,763,098 | | 8/1988 | Glenn et al. . |
| 4,815,472 | * | 3/1989 | Wise et al. ........................... 600/488 |
| 5,050,297 | | 9/1991 | Metzger . |
| 5,113,868 | * | 5/1992 | Wise et al. ........................... 600/488 |
| 5,207,103 | * | 5/1993 | Wise et al. ........................... 73/724 |
| 5,367,435 | | 11/1994 | Andros et al. . |
| 5,398,687 | | 3/1995 | Abell . |
| 5,421,080 | | 6/1995 | Bellavanca et al. . |
| 5,450,853 | | 9/1995 | Hastings et al. . |
| 5,715,827 | * | 2/1998 | Corl et al. ........................... 600/486 |
| 5,902,248 | * | 5/1999 | Millar et al. ........................ 600/485 |
| 6,019,728 | * | 2/2000 | Iwata et al. ......................... 600/486 |
| 6,106,476 | * | 8/2000 | Corl et al. ........................... 600/486 |

* cited by examiner

Primary Examiner—John P. Lacyk
Assistant Examiner—Navin Natnithithadha
(74) Attorney, Agent, or Firm—Wood, Herron & Evans, L.L.P.

(57) ABSTRACT

A catheter for sensing vertebrate conditions has plural piezoresistive sensors directly electrically coupled to discrete application specific integrated circuits. A mechano-responsive element is in pressure sensitive relationship with the piezoresistive sensor to act as a transfer medium through which vertebrate conditions such as pressure, temperature, water, glucose, and pH are transferred. Each integrated circuit is electrically coupled to a data acquisition system with monolithic circuitry in order to amplify and multiplex signals from multiple sensors.

23 Claims, 3 Drawing Sheets

CATHETER WITH MECHANO-RESPONSIVE ELEMENT FOR SENSING PHYSIOLOGICAL CONDITIONS

FIELD OF THE INVENTION

This invention relates to catheters. More specifically, this invention relates to catheters for sensing vertebrate conditions.

BACKGROUND OF THE INVENTION

Catheters known in the prior art have been used in humans and animals for diagnostic, monitoring and treatment purposes. Such catheters must be small and flexible in order to function without irritating a body part into which they are inserted. Catheters have been used to infuse medications or remove samples of tissue and fluid for analysis. Multi-lumen catheters have been used to infuse medication and remove samples at the same time.

If a sample must be removed for purposes of analysis, and taken to a laboratory for subsequent analysis, the delay in performing analysis and transmitting the data back to a doctor sometimes can be fatal to a patient. Catheters have also been used to form hydraulic columns for transmitting pressure readings to an external sensor. In pressure sensing catheters, the hydraulic column may have problems with air bubbles, kinks in the tubing, and blood clots affecting the reliability and accuracy of critical readings.

Catheters used for monitoring variations in blood pressure within a blood vessel include those using catheter tip transducers insertable into a blood vessel with the transducer providing direct pressure monitoring by transducing blood pressure at the region of interest. Such catheters have used a semiconductor material constructed and arranged with strain sensing beams for creating a proportionate electrical signal representative of the monitored pressure and transmitting the signal by electrical conductors through the length of the catheter to meters or the like located externally of the monitored body.

An example of such a catheter is seen in U.S. Pat. No. 4,274,423. This catheter includes a pressure sensor disposed within the end portion of a catheter. The pressure sensor uses a pressure sensitive diaphragm constructed from block of semiconductor material. The diaphragm is located adjacent a side port in the catheter housing connected to the end of the catheter with the port providing access to the pressure environment. The diaphragm is directly deflected relative to the pressure exerted thereon and the deflection is sensed by one or more strain gauges located within the diaphragm itself. The strain gauges are connected by conductors to a processor circuit located external of the catheter.

A concern with such catheters is to provide a transducer which is small, while also being sufficiently responsive to pressure variations to provide meaningful electrical output signals. The semiconductor block with the diaphragm or membrane of the type employed in U.S. Pat. No. 4,274,423, may well have a width on the order of 1.2 mm, which limits the size of the catheter and, hence, its application for use in measuring blood pressure and other conditions within a blood vessel.

U.S. Pat. No. 4,722,348, shows a pressure sensing catheter of small size, however, since the catheter body shown has side port pressure inlet apertures which are depressed into the catheter body, this catheter is susceptible to air bubbles being trapped within the pressure apertures, resulting in inaccurate sensor measurements. This catheter is also connected to a detector circuit located outside of the catheter.

SUMMARY OF THE INVENTION

This invention is directed to a catheter having a piezoresistive pressure sensor directly electrically coupled to an integrated circuit for measuring physiological conditions of a vertebrate. The physiological condition is measured by a pressure change which is directly related to the condition and that pressure is detected by the piezoresistive sensor which transmits an electrical impulse directly to the circuit.

In one form of the invention, a catheter with an elongated axis carries a conductive member coupled to plural piezoresistive sensors for measuring physiological conditions of a vertebrate. Each sensor is directly electrically coupled with a bonding pad to a discrete integrated circuit carried internally of the catheter.

In another form of the invention, the catheter has a mechano-responsive element in functional relationship with the piezoresistive sensor. The mechano-responsive element acts as a transfer medium between a vertebrate condition and the piezoresistive sensor which is directly electrically coupled to integrated circuit.

Various physiological vertebrate conditions, e.g., pressure, pH, glucose, water, and temperature, may be detected by the pressure responsive sensors of the catheter. These conditions are transmitted to a computer based data acquisition system. In a preferred embodiment, a stranded copper wire is connected to an application specific integrated circuit and a piezoresistive sensor coupled therewith internally of the catheter. The piezoresistive sensor is directly electrically coupled to the integrated circuit with a solder bonding pad by low temperature thermal compression bonding. In this preferred embodiment, the sensor has a trough in its top surface that receives therein a mechano-responsive element. The mechano-responsive element comprises a fluid or a gel that is sealed from coming into direct contact with the body by a permeable film which acts as a sheath over the piezoresistive sensor. The mechano-responsive element enables conditions such as pH, glucose, water, and temperature to be detected and the detecting signal to be converted into pressure which is sensed by the piezoresistive sensor and then thereby converted to an electrical impulse which is transmitted to the circuit for ultimate processing by a computer. Each sensing site is connected to other sensing sites with the stranded copper wire. Data received at a sensing site from a condition measured from a vertebrate body is transmitted to the data acquisition system via monolithic circuitry. That is, each circuit amplifies and multiplexes signals from plural sensors using a simple count and select scheme.

Other advantages of the invention will become more apparent to those of ordinary skill upon review of the following detailed description of the preferred embodiment taken in conjunction with the accompanying detailed drawings.

BRIEF DESCRIPTION OF THE DRAWINGS

FIG. 3 is a perspective cutaway view of the sensing site of FIG. 2A; and

DETAILED DESCRIPTION OF THE PREFERRED EMBODIMENT

Figure 1:
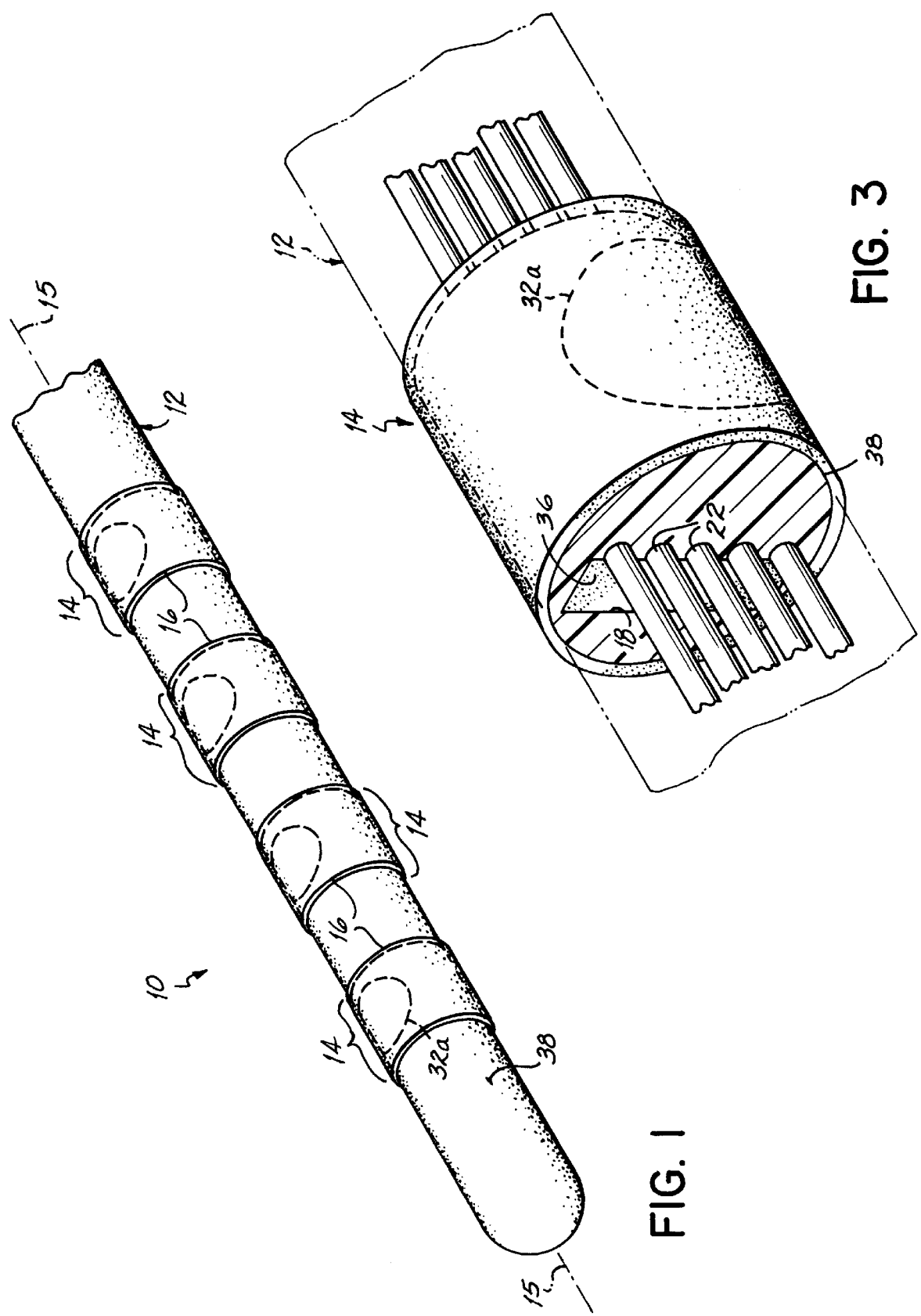
FIG. 1 is a perspective view of a catheter according to the present invention.

As seen in FIG. 1, a catheter 10 has a catheter body 12 with an elongated axis 15 having at least one sensing site 14. As will be used in the present description, a catheter 10 is generally an elongated tube or device for either measuring a physiological condition, or sampling a fluid or tissue. In the preferred embodiment, the catheter body 12 is made from a physiologically acceptable material, e.g., polyvinyl chlorate or silicone rubber. Such catheter bodies are available from Microvasive, Boston, Mass.

Each sensing site 14 is covered by a film 16 that prevents the sensing site 14 from coming into direct contact with a vertebrate body. As will be understood by those skilled in the art, the catheter 10 may be banded with the film 16 covering only the sensing site 14, or the film 16 may be formed as a sleeve covering the entire catheter body 12. In the preferred embodiment, the film 16 is made of silicon. In an alternative embodiment (FIG. 2A), the film 16 is permeable to allow conditions such as pH, glucose, temperature, and water to interact with the sensing site 14.

Figure 2:
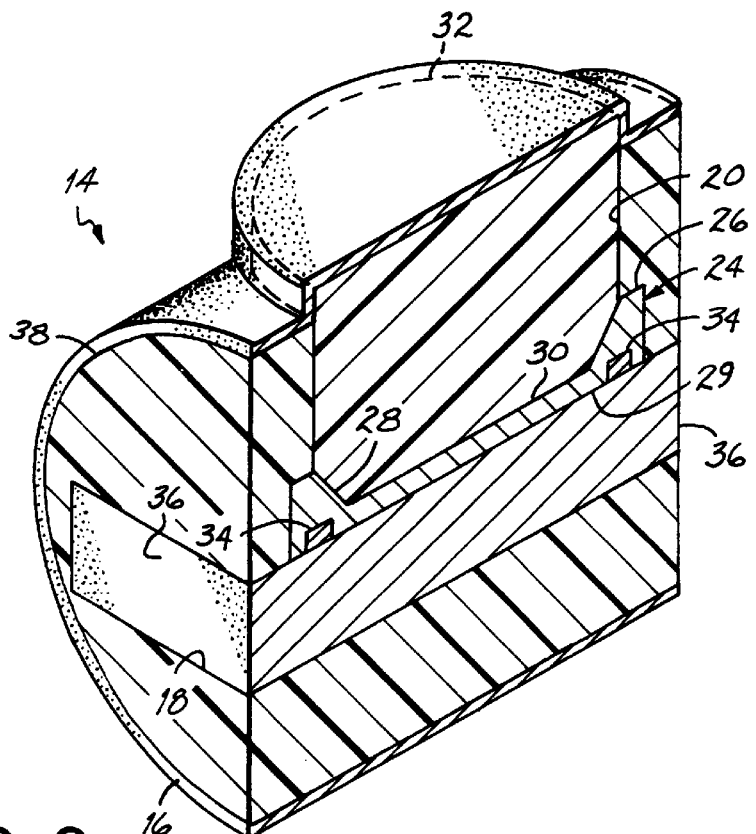
FIG. 2 is a perspective cutaway view of a single sensing site on the catheter of FIG. 1.
Figure 4:
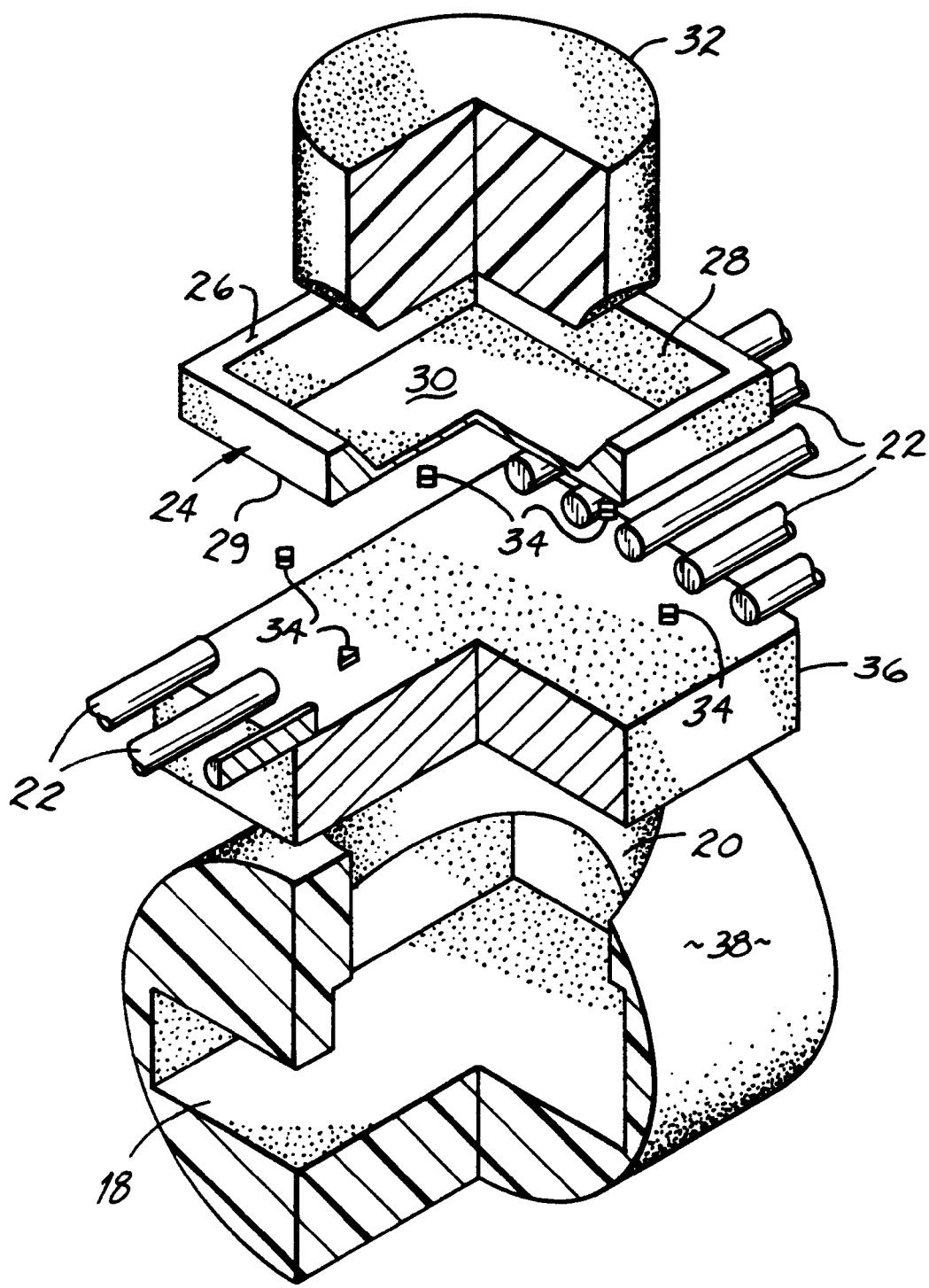
FIG. 4 is an exploded perspective view of the sensing site of FIG. 2.

As seen in FIG. 2, the catheter body 12 defines a lumen 18 in fluid communication with a catheter recess 20 defined in the catheter body 12. A conductive member 22 is carried in the lumen 18 and is approximately coextensive therewith (FIGS. 3 and 4). In the preferred embodiment, the conductive member 22 is stranded copper wire, however, those skilled in the art will understand that other conductive members 22 may be carried by the catheter body 12. In an alternative embodiment, solid core copper wire is used as the conductive member 22. In another alternative embodiment, copper traces (not shown) deposited on a non-conductive polymer strip (not shown) are used as the conductive member 22. The conductive member 22 carries power to and data from a piezoresistive sensor 24 that is acted on by a vertebrate condition. In the preferred embodiment, the sensor 24 is about 1.74 to 1.76 mm long, about 1.74 to 1.76 mm wide, and about 0.24 to 0.26 mm deep. The sensor 24 has a bottom surface 29 and a top surface 26 defining a trough 28 therein. The trough 28 has a trough floor 30 that is deformable according to pressures exerted upon the floor 30 by a mechano-responsive element, i.e., a fluid 32 or a gel 32a. As is used in the present description, the term "mechano-responsive element" will be understood to mean an element 32, 32a that has a measurable physical response in proportion to a condition influencing the element 32, 32a.

In the preferred embodiment, the sensor 24 is made from piezoresistive material, e.g., silicon and silicon dioxide. The sensor 24 has at least one bonding pad 34 affixed to the bottom surface 29. In the preferred embodiment, the bonding pad 34 is a eutectic solder having about a 63/37 lead/tin composition. In an alternative embodiment, indium solder is used as for the bonding pad 34. In another alternative embodiment, a conductive polymer such as silver epoxy is used for the bonding pad 34.

The sensor 24 is bonded to an application specific integrated circuit 36 by a method of low temperature thermal compression bonding known in the art. The sensor 24 is thereby directly electrically coupled to the circuit 36 with the bonding pads 34. The circuit 36 is directly electrically coupled to the conductive member 22 carried by the catheter body 12. In the preferred embodiment, the conductive member 22 is comprised of about two to six stranded copper wires bonded to the integrated circuit 36 that are soldered to the circuit 36. In an alternative embodiment, the conductive member 22 is attached to the circuit 36 by press contacting. In the most preferred embodiment, the conductive member 22 has separate high and low power input wires, separate high and low signal output wires, and a clock wire used as a toggle to step through plural sensing sites 14.

The sensor 24 is positioned within the catheter body 12 so that the trough 28 opens upwardly through the catheter recess 20. In the preferred embodiment, the catheter 10 has up to about thirty-two sensing sites 14 positioned along the catheter axis 15. Each sensing site 14 has a sensor 24 directly electrically coupled to a circuit 36 by at least one bonding pad 34. In the preferred embodiment, catheter 10 is connected to a computer based data acquisition system (not shown) that supplies power to and receives vertebrate condition data from the sensing site 14 via the conductive member 22. The circuit 36 is monolithically incorporated with the sensor 24 so the circuit 36 amplifies an electrical signal from the sensor 24 and multiplexes signals received from multiple sensors 24 by a simple count and select scheme known in the art so as to minimize the number of conductive members 22 affixed to the circuit 36 and, thereby, reduce the diameter of the catheter 10.

The mechano-responsive element, i.e., a fluid 32 or a gel 32a, is located in the sensor trough 28 so that it substantially fills the trough 28 and the catheter recess 20. In the preferred embodiment, the fluid 32 is silicon oil, used to measure vertebrate pressures. The fluid 32 rises above the outer surface 38 of the catheter body 12 and is sealed with the film 16 so that the fluid 32 bulges above the surface 38 so that no air bubbles are trapped at the sensing site 14, thereby substantially eliminating measurement error caused by trapped air bubbles. The catheter 1 0 with the fluid 32 is able to measure pressures in the range of about −50 to +300 mmHg exerted upon the sensing site 14. Sensed pressure is transferred via the fluid 32 to the sensor floor 30, which deforms in proportion to the pressure exerted.

Figure 2A:
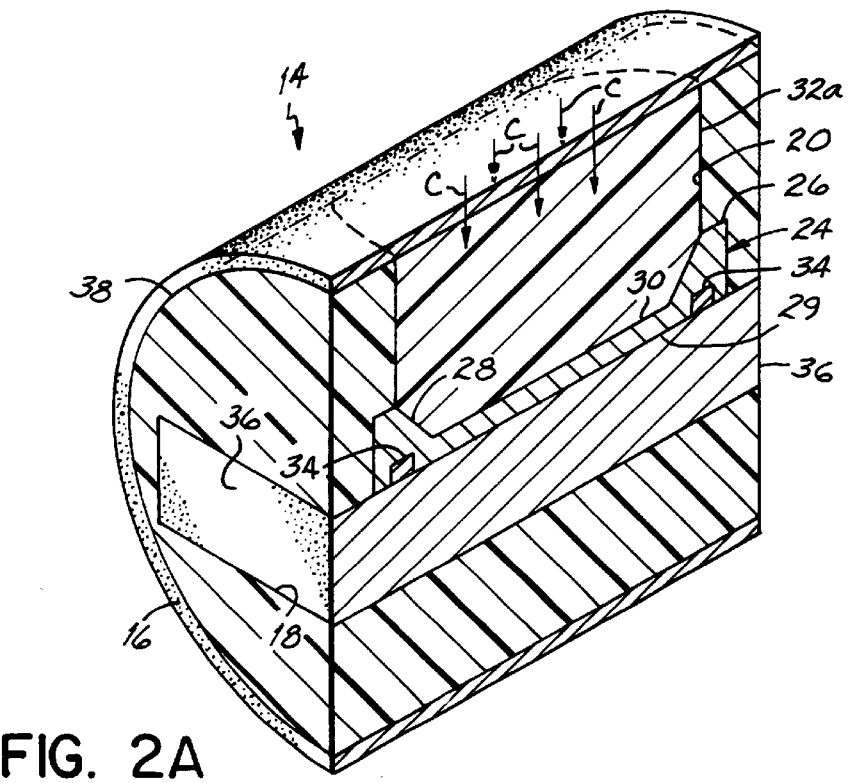
FIG. 2A is an alternative embodiment of the sensing site of FIG. 2.

In an alternative embodiment, as seen in FIG. 2A, the gel 32a, e.g., a polyester gel, a polyamide gel, or a hydrogel, is responsive to non-pressure vertebrate conditions, e.g., temperature, water, glucose, pH. The gel 32a is placed in the sensor trough 28 and catheter recess 20, and sealed by the catheter film 16, so it does not bulge above the outer surface 38 of the catheter body 12. The gel 32a generally swells or shrinks in volume when acted on by non-pressure conditions, thereby changing pressure the gel 32a exerts on the sensor floor 30 in proportion to the vertebrate condition. In this embodiment, the catheter film 16 covering the sensing site 14 is permeable to allow the vertebrate condition to interact with the gel 32a, as shown by directional arrows C (FIG. 2A). Each sensing site 14 on a catheter 10 having plural sensing sites 14 can measure a different vertebrate condition by multiplexing signals from different sensing sites 14 and using a simple count and select scheme. For example, temperature may be measured in conjunction with any of the other measurements by interrogation of the circuit elements employed in a temperature circuit. For example, diodes with a negative temperature coefficient are included as part of a constant voltage delivery circuit contained on the circuit 36. These diodes deliver an increase in voltage with temperature to a bridge network. The diodes can be monitored to measure temperature.

Other variations of the structure will be apparent to a person of ordinary skill in the art in view of other patents such as U.S. Pat. Nos. 4,274,423 and 4,722,348, the disclosures of which are incorporated herein by reference.

Additional advantages and modifications will readily appear to those skilled in the art. The invention in its broader aspects is therefore not limited to the specific detail, representative apparatus and illustrative example shown and described. This has been a description as the present invention is currently known. However, the invention itself should only be defined by the appended claims.

What is claimed is:

1. A catheter for measuring a physiological condition of a vertebrate, comprising:
   an elongated catheter having a recess;
   a conductive member carried by said catheter;
   a piezoresistive pressure sensor having a top surface, and a bottom surface, said sensor defining a trough in said top surface, said pressure sensor located in said recess;
   a mechano-responsive element comprising one of a fluid and a gel encapsulated in said trough to transfer the condition acting upon said element to said sensor and a permeable membrane encapsulating said mechano-responsive element in said trough; and
   a circuit integrated with said conductive member, said pressure sensor being directly electrically coupled to said circuit, said sensor and circuit for measuring the physiological condition.

2. The catheter of claim 1, wherein said gel is encapsulated in said trough for direct communication with the condition being sensed.

3. The catheter of claim 2, wherein said mechano-responsive element is sensitive to the condition selected from the group consisting of pressure, water, pH, glucose, and temperature.

4. The catheter of claim 1, further comprising at least one bonding pad affixed to said pressure sensor bottom surface, said pressure sensor being bonded to said circuit.

5. The catheter of claim 1, wherein said pressure sensor is made from silicon and silicon dioxide.

6. The catheter of claim 1, wherein said fluid is silicon oil.

7. The cather of claim 1, wherein said gel is selected from the group consisting of a polyester gel, a polyamide gel, and a hydrogel.

8. The catheter of claim 1, wherein said catheter is for measuring pressures internal of a vertebrate body in the range of about −50 to +300 mmHg.

9. A catheter for measuring a physiological condition of a vertebrate, comprising:
   a catheter having a recess;
   a conductive member carried by said catheter, said conductive member being conductible to electric signals;
   a circuit directly electrically coupled with said conductive member;
   a piezoresistive pressure sensor having a bottom surface, and a top surface defining a trough therein, said pressure sensor being directly electrically coupled to said circuit and located in said recess volume so that said trough opens upwardly through said recess, said sensor and circuit for measuring the physiological condition;
   a mechano-responsive element encapsulated in said trough and said recess;
   a permeable membrane for encapsulating said mechano-responsive element;
   a bonding pad affixed to said bottom surface of said pressure sensor, for bonding said pressure sensor to said integrated circuit; and
   a data acquisition system to power said catheter, said system receivable to electrical signals proportional to at least one vertebrate condition selected from the group consisting of pressure, pH, water, glucose, and temperature, wherein the condition acts upon said mechano-responsive element and is transferred to said pressure sensor.

10. The catheter of claim 9, said conductive member comprising a non-conductive cable and at least one metal trace deposited on said cable.

11. The catheter of claim 10, wherein said metal trace is copper.

12. The catheter of claim 9, said conductive member comprising at least one conductive wire.

13. The catheter of claim 12, wherein said at least one conductive wire is copper.

14. The catheter of claim 12, wherein said at least one conductive wire is selected from the group consisting of stranded wire and solid core wire.

15. The catheter of claim 9, wherein said bonding pad material is selected from the group consisting of lead, tin, and indium.

16. The catheter of claim 9, wherein said bonding pad is a conductive polymer.

17. The catheter of claim 16, wherein said bonding pad is silver epoxy.

18. The catheter of claim 9, wherein said mechano-responsive element is silicon oil.

19. The catheter of claim 9, wherein said mechano-responsive element is selected from the group consisting of a polyester gel, a polyamide gel, and a hydrogel.

20. The catheter of claim 9, wherein said catheter is for measuring pressures internal of a human body in the range of about −50 to +300 mmHg.

21. The catheter of claim 9, wherein said catheter is for measuring at least one condition selected from the group consisting of pressure, pH, temperature, water, and glucose.

22. The catheter of claim 9, wherein said piezoresistive sensor is made from the group consisting of silicon and silicon dioxide.

23. A catheter for measuring a physiological condition of a vertebrate, comprising:
   a physiologically acceptable catheter having an outside diameter of about 2 mm, said catheter having a recess and an elongated axis;
   at least one stranded copper wire carried by said catheter, said wire being conductible to electricity, wherein said catheter carries about two to six wires;
   a circuit directly electrically coupled with said conductive member;
   a pressure sensor having a length of about 1.74 to 1.76 mm, a width of about 1.74 to 1.76 mm, a depth of about 0.24 to 0.26 mm, a bottom surface, and a top surface defining a trough therein, said pressure sensor being located in said recess and electrically coupled to said integrated circuit so that said trough opens upwardly through said recess, wherein said sensor is made from the group consisting of silicon and silicon dioxide, said sensor and said circuit for measuring the physiological condition, wherein said catheter has up to about thirty-two sensors spaced along said elongated axis;
   at least one pad bonding said bottom of said sensor by low temperature thermal compression bonding to said integrated circuit, wherein said pad is selected from the group consisting of lead and tin;

a mechano-responsive element received in said trough and said recess, wherein said element is silicon oil;

a permeable membrane for sealing said mechano-responsive element in said recess; and a data acquisition system to power said catheter and to receive electrical signals proportional to vertebrate body pressures in the range of about −50 to +300 mmHg exerted upon said mechano-responsive element and transferred to said pressure sensor.

* * * * *